(12) United States Patent
Eisenberg et al.

(10) Patent No.: US 6,512,981 B1
(45) Date of Patent: Jan. 28, 2003

(54) PROTEIN FOLD RECOGNITION USING SEQUENCE-DERIVED PREDICTIONS

(75) Inventors: David Eisenberg, Los Angeles, CA (US); Daniel Fischer, Lehavim (IL)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/071,279

(22) Filed: May 1, 1998

Related U.S. Application Data (60) Provisional application No. 60/045,273, filed on May 1, 1997.

(51) Int. Cl.⁷ .............................. G06F 19/00; C12Q 1/00
(52) U.S. Cl. ............................................. 702/19; 435/4
(58) Field of Search ...................... 530/350; 364/411.1, 364/175, 183, 194, 468.09; 702/19; 435/4

(56) References Cited

U.S. PATENT DOCUMENTS 5,436,850 A * 7/1995 Eisenberg et al. .......... 364/496
5,878,373 A * 3/1999 Cohen et al. ................. 702/22

OTHER PUBLICATIONS

Russell et al., "Protein fold recognition by mapping predicted secondary structures" J. Mol. Biol. vol. 259, pp. 349–365, 1996.*

Kreisberg et al., "Paired natural cysteine mutation mapping: Aid to constraing models of protein structure" Preotein Science (1995), vol. 4, pp. 2405–2410.*

* cited by examiner

*Primary Examiner*—John S. Brusca
(74) *Attorney, Agent, or Firm*—Fish & Richardson P.C.

(57) ABSTRACT

A computer-assisted method for assigning an amino acid probe sequence to a known three-dimensional protein structure. In particular, the invention includes a method for using the amino acid sequence of a probe plus sequence-derived properties of the probe in making fold assignments. The method includes inputting into a computer system a string $p_1, p_2 \ldots p_n$ describing the amino acid sequence of the probe sequence and at least one sequence-derived property for the probe sequence; inputting into a computer system a string $t_1, t_2 \ldots t_m$ of structural properties for each member of a library of known 3D structures; executing an alignment algorithm in the computer to compute an alignment score indicating the optimal alignment of the string $p_1, p_2 \ldots p_n$ to each string $t_1, t_2 \ldots t_m$ by applying a combined compatibility function $g(p_i, t_j)$; determining the statistical significance of each alignment score to determine a best-fit alignment score; and applying the best-fit alignment score to indicate or select the corresponding 3D protein structure from the library for output to a user. The invention includes a computer program implementation of such a method.

27 Claims, 7 Drawing Sheets

FIG. 1

| Class/fold | Probe seq. | Target struct. | Seq. Id. | Rank $g^s_{gon}$ | $g^p_{gon}$ |
|---|---|---|---|---|---|
| α: 13 pairs ||||||
| Globin-Like | 1dxth | 1hbg | 19 | 1 | 1 |
|  | 1cpcl | 1cola | 17 | 1 | 1 |
| Cytochrome | 1c2ra | 1ycc | 23 | 1 | 1 |
|  | 2mtac | 1ycc | 15 | 5 | 2 |
| Helix Bundle | 1bbha | 2ccya | 21 | 1 | 1 |
|  | 1bgeb | 1gmfa | 12 | 4 | 1 |
|  | 1rcb | 1gmfa | 21 | 8 | 6 |
|  | 1acp | 256ba | 14 | 6 | 2 |
| EF-Hand | 1osa | 4cpv | 24 | 1 | 1 |
|  | 2sas | 2scpa | 17 | 1 | 1 |
| Other | 1hom | 1lfb | 19 | 2 | 2 |
|  | 1lgaa | 2cp | 16 | 1 | 1 |
|  | 2hpda | 2cpp | 18 | 1 | 1 |
| β: 25 pairs ||||||
| IG | 1fcla | 2fb4h | 19 | 1 | 1 |
|  | 2fbjl | 8fabb | 22 | 1 | 1 |
| IG-Like | 1cid | 2rhe | 13 | * | * |
|  | 1pfc | 3hlab | 22 | 1 | 1 |
|  | 1ten | 3hhrb | 18 | * | * |
|  | 1tlk | 2rhe | 24 | 2 | 1 |
|  | 3cd4 | 2rhe | 25 | 1 | 1 |
|  | 3hlab | 2rhe | 15 | * | 1 |
| Cupredoxin | 1aaj | 1paz | 31 | 1 | 1 |
|  | 1afna | 1aoza | 19 | 1 | 1 |
|  | 2azaa | 1paz | 11 | * | * |
| Virus | 4sbva | 2tbva | 19 | 1 | 1 |
|  | 1bbt1 | 2plv1 | 20 | 1 | 1 |
| Lectin-Like | 1saca | 1ayh | 14 | * | * |
| OB Fold | 1ltsd | 1bova | 19 | 2 | 1 |
| Trefoil | 1tic | 4fgf | 14 | * | * |
|  | 8ilb | 4fgf | 18 | 1 | 1 |
| Trypsin | 1arb | 4ptp | 20 | 1 | 1 |
|  | 2sga | 4ptp | 21 | 1 | 1 |
|  | 2snv | 4ptp | 15 | * | * |
| Lipocalin | 1mdc | 1ife | 21 | 1 | 1 |
|  | 1mup | 1rbp | 14 | 1 | 1 |
| Propeller | 1sim | 1nsba | 12 | * | 1 |
| Other β | 1caub | lcaua | 18 | 1 | 1 |
|  | 1omf | 2por | 17 | 1 | 1 |

FIG. 2A

| Class/fold | Probe seq. | Target struct. | Seq. Id. | Rank $g^s_{gon}$ | $g^p_{gon}$ |
|---|---|---|---|---|---|
| α/β: 20 pairs | | | | | |
| TIM Barrel | 1chra | 2mnr | 20 | 1 | 1 |
| | 2mnr | 4enl | 18 | * | 1 |
| | 3rubl | 6xia | 18 | 2 | 8 |
| Hyrdolase | 1crl | 1ede | 17 | * | * |
| | 1taha | 1tca | 16 | 1 | 1 |
| Thieredoxin | 1aba | 1ego | 21 | 1 | 1 |
| | 1dsba | 2trxa | 13 | 5 | 2 |
| | 1gpla | 2trxa | 17 | * | * |
| Ribonuclease H | 1atna | 1atr | 15 | * | 1 |
| | 1hrba | 1rnh | 24 | 1 | 1 |
| Open Sheet | 3chy | 4fxn | 14 | * | * |
| | 1ak3a | 1gky | 17 | 2 | 2 |
| | 1gky | 3adk | 24 | 1 | 1 |
| | 2cmd | 6ldh | 23 | 1 | 1 |
| | 1eaf | 4cla | 21 | 2 | 1 |
| | 2gbp | 2liv | 16 | 5 | 1 |
| | 1mioc | 1minb | 16 | 1 | 1 |
| | 2pia | 1fnr | 18 | 1 | 1 |
| | 1gal | 3cox | 18 | 1 | 1 |
| | 1npx | 3grs | 20 | 1 | 1 |
| α+β: 7 pairs | | | | | |
| UB Fold | 1fxia | 1ubq | 18 | * | 2 |
| Cystatin | 1cew | 1mola | 10 | * | * |
| | 1stfi | 1mola | 8 | 4 | 1 |
| SH2 | 2pna | 1shaa | 29 | 1 | 1 |
| Other α+β | 2sara | 9rnt | 12 | 1 | 1 |
| | 1onc | 7rsa | 26 | 1 | 1 |
| | 5fd1 | 2fxb | 21 | 1 | 1 |
| Other: 3 pairs | | | | | |
| Multidomain Mixed α&β | 2hhma | 1fbpa | 13 | 1 | 1 |
| Small | 1hip | 2hipa | 19 | 1 | 1 |
| | 1isua | 2hipa | 16 | 1 | 1 |

*FIG. 2B*

| Compat. Function | | % Target folds | Overall score S* | | | | | | % improvement | |
|---|---|---|---|---|---|---|---|---|---|---|
| Sec. Str. | Name | at rank 1 | .3 | .4 | .5 | .6 | .7 | .8 | Score S* | Folds in rank 1 |
| | $g_0$: Secondary Structure Only (no sequence) | | | | | | | | | |
| None | $g_0^s$ | N.A. | | | | | | | - | - |
| Predicted | $g_0^p$ | 38 | ********** | | | | | | 22 | 31 |
| True | $g_0^r$ | 50 | *************** | | | | | | | |
| | $g_{bow}$: Bowie's 3D-1D Scores | | | | | | | | | |
| None | $g_{bow}^s$ | 37 | ********* | | | | | | - | - |
| Predicted | $g_{bow}^p$ | 46 | *************** | | | | | | 22 | 24 |
| True | $g_{bow}^r$ | 56 | ****************** | | | | | | 16 | 23 |
| | $g_{id}$: Identity Matrix | | | | | | | | | |
| None | $g_{id}^s$ | 43 | *********** | | | | | | - | - |
| Predicted | $g_{id}^s$ | 54 | ***************** | | | | | | 23 | 28 |
| True | $g_{id}^s$ | 72 | ************************ | | | | | | 24 | 32 |
| | $g_{blo}$: Blossum Matrix | | | | | | | | | |
| None | $g_{blo}^s$ | 54 | ***************** | | | | | | - | - |
| Predicted | $g_{blo}^p$ | 65 | ********************* | | | | | | 15 | 19 |
| True | $g_{blo}^r$ | 73 | ************************ | | | | | | 11 | 14 |
| | $g_{gon}$: Gonnet Matrix | | | | | | | | | |
| None | $g_{gon}^s$ | 59 | ****************** | | | | | | - | - |
| Predicted | $g_{gon}^p$ | 71 | ************************ | | | | | | 16 | 20 |
| True | $g_{gon}^r$ | 76 | ************************** | | | | | | 5 | 8 |
| | | | .3 | .4 | .5 | .6 | .7 | .8 | | |

FIG. 3

Probe sequence: mandelate racemase, 2mnr. Class α/β, TIM barrel.
(↓ = expected target fold: enolase, 4enl; 18% sequence identity)

2mnr without predicted secondary structure

2mnr with predicted secondary structure

FIG. 4A

Probe sequence: sialidase, 1sim. Class β, propeller.
(↓ = expected target fold: neuraminidase, 1nsba; 12% sequence identity)

1sim without predicted secondary structure

1sim with predicted secondary structure

PROTEIN FOLD RECOGNITION USING SEQUENCE-DERIVED PREDICTIONS

CROSS REFERENCE TO RELATED APPLICATIONS

This application claims the benefit of U.S. Patent Application Serial No. 60/045,273, filed May 1, 1997.

TECHNICAL FIELD

This invention relates to a computer-assisted method for identifying protein sequences that fold into a known three-dimensional structure, and more particularly to a computer-assisted method for assigning an amino acid probe sequence to a known three-dimensional protein structure.

BACKGROUND

Proteins (or polypeptides) are linear polymers of amino acids. The polymerization reaction which produces a protein results in the loss of one molecule of water from each amino acid, and hence proteins are often said to be composed of amino acid "residues." Natural protein molecules may contain as many as 20 different types of amino acid residues, each of which contains a distinctive side chain. The particular linear sequence of amino acid residues in a protein defines the primary sequence, or primary structure, of the protein. The primary structure of a protein can be determined with relative ease using known methods.

Proteins fold into a three-dimensional structure. The folding is determined by the sequence of amino acids and by the protein's environment. Examination of the three-dimensional structure of numerous natural proteins has revealed a number of recurring patterns, or secondary structure. Secondary structures known as alpha helices, parallel beta sheets, and anti-parallel beta sheets are the most common observed. A description of such secondary structures is provided by Dickerson, R. E., et al. in *The Structure and Action of Proteins,* W. A. Benjamin, Inc. Calif. (1969). The helices, sheets, and turns of a protein's secondary structure pack together to produce the folded three-dimensional, or tertiary, structure of the protein.

In the past, the three-dimensional structure of proteins has been determined in a number of ways. Perhaps the best known way of determining protein structure involves the use of the technique of x-ray crystallography. A general review of this technique can be found in *Physical Bio-chemistry,* Van Holde, K. E. (Prentice-Hall, N.J. 1971), pp. 221–239, or in *Physical Chemistry with Applications to the Life Sciences,* D. Eisenberg & D. C. Crothers (Benjamin Cummings, Menlo Park 1979). Using this technique, it is possible to elucidate three-dimensional structure with good precision. Additionally, protein structure may be determined through the use of the techniques of neutron diffraction, or by nuclear magnetic resonance (NMR). See, e g., *Physical Chemistry,* 4th Ed. Moore, W. J. (Prentice-Hall, N.J. 1972) and *NMR of Proteins and Nucleic Acids,* K. Wüthrich (Wiley-Interscience, NY 1986).

The biological properties of proteins depend directly on the protein's three-dimensional (3D) conformation. The 3D conformation determines the activity of enzymes, the capacity and specificity of binding proteins, and the structural attributes of receptor molecules. Because the three-dimensional structure of a protein molecule is so significant, it has long been recognized that a means for readily determining a protein's three-dimensional structure from its known amino acid sequence would be highly desirable.

However, it has proved extremely difficult to make such a determination. One difficulty is that each protein has an astronomical number of possible conformations (about $10^{16}$ for a small protein of 100 residues; see K. A. Dill, *Biochemistry,* 24, 1501–1509, 1985), and there is no reliable method for picking the one conformation stable in aqueous solution. A second difficulty is that there are no accurate and reliable force laws for the interaction of one part of a protein with another part, and with water. Proteins exist in a dynamic equilibrium between a folded, ordered state and an unfolded, disordered state. These and other factors have contributed to the enormous complexity of determining the most probable relative 3D location of each residue in a known protein sequence.

The protein folding problem, the problem of determining a protein's three-dimensional tertiary structure from its amino acid sequence, or primary structure, has defied solution for over 30 years. In the last decade, however, the increase in the number of known protein sequences, and the fact that many sequences have been found to fold into the same basic three-dimensional structure, have focused attention on a related problem: the inverse protein folding problem. The inverse protein folding problem asks, given a known three dimensional protein structure, which amino acid sequences fold into that structure?

As a result of the molecular biology revolution, the number of known protein sequences is about 50 times greater than the number of known three-dimensional protein structures. This disparity hinders progress in many areas of biochemistry because a protein sequence has little meaning outside the context of the three-dimensional structure. The disparity is less severe than the numbers might suggest, however, because different proteins often adopt similar three-dimensional folds. As a result, each new protein structure can serve as a model for other protein structures. These structural similarities occur because the current array of protein structures probably evolved from a small number of primordial folds. If the number of folds is indeed limited, it is possible that x-ray crystallographers and NMR spectroscopists may eventually describe examples of essentially every fold. In that event, protein structure prediction theoretically would reduce, at least in crude form, to the inverse protein folding problem—the problem of identifying which fold in this limited repertoire a particular amino acid sequence adopts. Thus, protein fold recognition aims to assign each new amino acid sequence to the known 3D fold that the sequence most closely resembles.

The inverse protein folding problem is most often approached by seeking sequences that are similar to the sequence of a protein whose structure is known. If a sequence relationship can be found, it can often be inferred that the protein of known sequence but unknown structure adopts a fold similar to the protein of known structure. The strategy works well for closely related sequences, but structural similarities can go undetected as the level of sequence identity drops below about 25 percent.

A more direct attack on the inverse protein folding problem has been to search for sequences that are compatible with a given structure. In this "tertiary template" method, the backbone of a known protein structure—the amino acid residues less the side chains—is kept fixed and the side-chains in the protein core are then replaced and tested combinatorially by computer, to find which combination of new side-chains could fit into the core. A set of core sequences is thereby enumerated that could in principle be tolerated in the protein structure. In this manner, the method of tertiary templates provides a direct link between possible three-dimensional structure and known sequence. See Ponder & Richards, *J. Mol. Biol.*, 93, 775–791 (1987).

The rules used to relate one-dimensional amino acid sequences to possible three-dimensional structures in the tertiary template method may be excessively rigid. Proteins that fold into similar structures can have large differences in the size and shape of residues at equivalent positions. These changes are tolerated not only because of replacements or movements in nearby side-chains, but also as a result of shifts in the protein backbone. Moreover, insertions and deletions in the amino acid sequence, which are commonly found in related protein structures, are not considered in the implementation of tertiary templates. To describe realistically the sequence requirements of a particular fold, the constraints of a rigid backbone and a fixed spacing between core residues must somehow be relaxed.

Another approach, suggested by work done by one of the present inventors, is a profile method that characterizes the amino acid sequences of families of proteins aligned by sequence or structural similarities. The profile method builds a table of weighted values that reflect the frequency that amino acid residues are likely to be located at a particular position in the sequence of amino acids forming the proteins. The profile table thus characterizes the entire family of proteins upon which the table is based. A target amino acid sequence is compared to the profile, using a known dynamic programming method, to determine a final "best fit" score. Insertions and deletions of amino acids in the target sequence are provided for by appropriate "gap opening" and "gap extension" penalties that affect the final score. See Gribskov et al., *Proc. Natl. Acad. Sci. U.S.A.*, 84, 4355 (1987); Gribskov et al., *CABIOS* 4, (1988); Gribskov & Eisenberg, in "Techniques in Protein Chemistry" (T. E. Hugli, ed.), p. 108. Academic Press, San Diego, Calif., 1989; Gribskov et al., *Meth. in Enz.* 183, 146 (1990).

The profile method is useful for learning whether a target protein sequence belongs to a known family of sequences, and some inferences can be made that the target sequence has a three-dimensional structure similar to the structures of the known family of sequences. However, the profile method does not directly take into account specific structural characteristics of the known family of target sequences, since the profile table is constructed based only upon alignments of amino acid sequences within selected proteins of known structure. Thus, a large amount of information inherent in a known structure is simply ignored in a sequence profile.

Bowie et al. developed an alternative method to the technique of assigning a new sequence to a known 3D fold by establishing similarity between the sequence to some sequence of known structure: score the compatibility of the new sequence against known 3D structures. Bowie et al. "A Method to Identify Protein Sequences that Fold into a Known Three-dimensional Structure", *Science* 253: 164–170 (1991). See also U.S. Pat. No. 5,436,850, entitled "Method to Identify Protein Sequences that Fold into a Known Three-dimensional Structure", issued Jul. 25, 1995, which is hereby incorporated by reference.

Since then, a variety of fold-recognition methods have been published, and several reviews on these methods have appeared. The approaches used differ in at least one of the components of fold recognition, namely: the representation of the protein, the function used to evaluate the compatibility between the unknown probe sequence and a fold, the algorithm used to search for the optimal alignment, the way ranking is computed, and the way significance is assessed.

More particularly, in sequence comparison fold recognition, compatibility of sequence to structure is assessed by optimally aligning the sequence of interest (the probe sequence) to each structure in a library of known folds (the target structures). The compatibility is computed by adding the compatibility score of each aligned position of probe to target and subtracting a penalty for any gaps in the alignment. The compatibility score can be defined by a one-positional compatibility function, $f(p_i, t_j)$, where $p_i$ represents the ith position of the probe sequence, and $t_j$ represents the jth position of the target structure. The value $t_j$ refers to some structural properties of residue j in the target structure, such as the local secondary structure, the solvent accessibility, the polarity, or the amino acid type (see, e.g., Bowie et al., supra). The value $t_j$ can also encode other information, such as some structural properties of neighboring residues. Thus, various compatibility functions describe a variety of structural properties for $t_j$. However, sequence comparison methods consider only the amino acid sequence of the probe sequence; that is, $p_i$ refers exclusively to the amino acid type at position i.

Thus, the basic difference between straight sequence comparison and sequence comparison fold recognition lies in the type of information used: in straight sequence comparison, a probe sequence is aligned to the sequences of the proteins in a library; in sequence comparison fold recognition, a probe sequence is aligned to some structural properties of the proteins in a library of known target 3D structures.

SUMMARY

The inventors have recognized that, with the increasing size of sequence databases, users are likely to find several homologues of a probe sequence to known 3D structures, and thus derive multiple alignments from such databases. From multiple alignments, sequence-derived properties (such as secondary structure, solvent accessibility, and hydrophobic moments) for the probe sequences can be predicted with accuracies greater than 70%. The inventors have recognized that such predictions of sequence-derived properties may be used to improve the accuracy of fold recognition algorithms. Accordingly, the present invention is directed to a method for using the amino acid sequence of a probe plus sequence-derived properties of the probe in making fold assignments. The method includes a computer-assisted procedure for assigning target amino acid sequences to known target 3D fold structures.

More particularly, in one aspect the invention includes a computer-assisted method for assigning an amino acid probe sequence to a known three-dimensional protein structure, including the steps of inputting into a computer system a string $p_1, p_2 \ldots p_n$ describing the amino acid sequence of the probe sequence and at least one sequence-derived property for the probe sequence; inputting into a computer system a string $t_1, t_2 \ldots t_m$ of structural properties for each member of a library of known 3D structures; executing an alignment algorithm in the computer to compute an alignment score indicating the optimal alignment of the string $p_1, p_2 \ldots p_n$ to each string $t_1, t_2 \ldots t_m$ by applying a combined compatibility function $g(p_i, t_j)$; determining the statistical significance of each alignment score to determine a best-fit alignment score; and applying the best-fit alignment score to indicate or select the corresponding 3D protein structure from the library for output to a user. The invention includes a computer program implementation of such a method.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

Overview

In protein fold recognition, the object is to assign a probe amino acid sequence of unknown structure to one of a library of target 3D structures. Correct assignment depends on effective scoring of the probe sequence for its compatibility with each of the target structures. In accordance with the invention, sequence-derived properties of the probe sequence (such as the secondary structure, solvent accessibility, and hydrophobic moments of the probe sequence) are used in addition to the amino acid sequence of the probe to assign the probe to a known 3D fold structure. In particular, the invention defines new compatibility functions that combine previously developed amino acid-to-structure compatibility scores (such as the 3D-1D scores of Bowie et al., supra, or sequence-sequence replacement tables) with sequence-derived predicted properties-to-structure compatibility functions. In the new combined compatibility functions, $p_i$, instead of referring exclusively to the ith amino acid of the probe, also includes the predicted structural properties of the probe.

The effect on fold assignment of adding predicted sequence-derived properties of the probe sequence can be evaluated by using a benchmark set of proteins. For such testing, the 3D structures of the probe sequences of the benchmark are actually known, but are ignored for purposes of evaluating the accuracy of the inventive method. The results show that inclusion of predicted secondary structure alone in accordance with the invention improves fold assignment accuracy by about 25%. The results also show that, if the true secondary structure of the probe sequence were known, correct fold assignment would increase by an additional 8–32%. Thus, incorporating sequence-derived predictions significantly improves assignment of sequences to known 3D folds.

TABLE 1 summarizes the differences in information used by the prior techniques of sequence comparison and conventional fold recognition in comparison to the invention (last column); + indicates the information is used; (+) indicates the information is used in some of the methods:

TABLE 1

| | Method | | |
|---|---|---|---|
| Information used | Sequence comparison | Fold recognition | Fold recognition with sequence-derived properties |
| Probe Sequence | | | |
| Amino acid sequence | + | + | + |
| Multiple alignment | + | | + |
| Sequence-derived properties (e.g., predicted secondary structure, predicted solvent accessibility) | | | + |
| Target Fold | | | |
| Amino acid sequence | + | (+) | + |
| Multiple alignment | | (+) | + |
| Structural properties (e.g., known secondary structure, known solvent accessibility) | | + | + |

Preferred Embodiment

Figure 1:
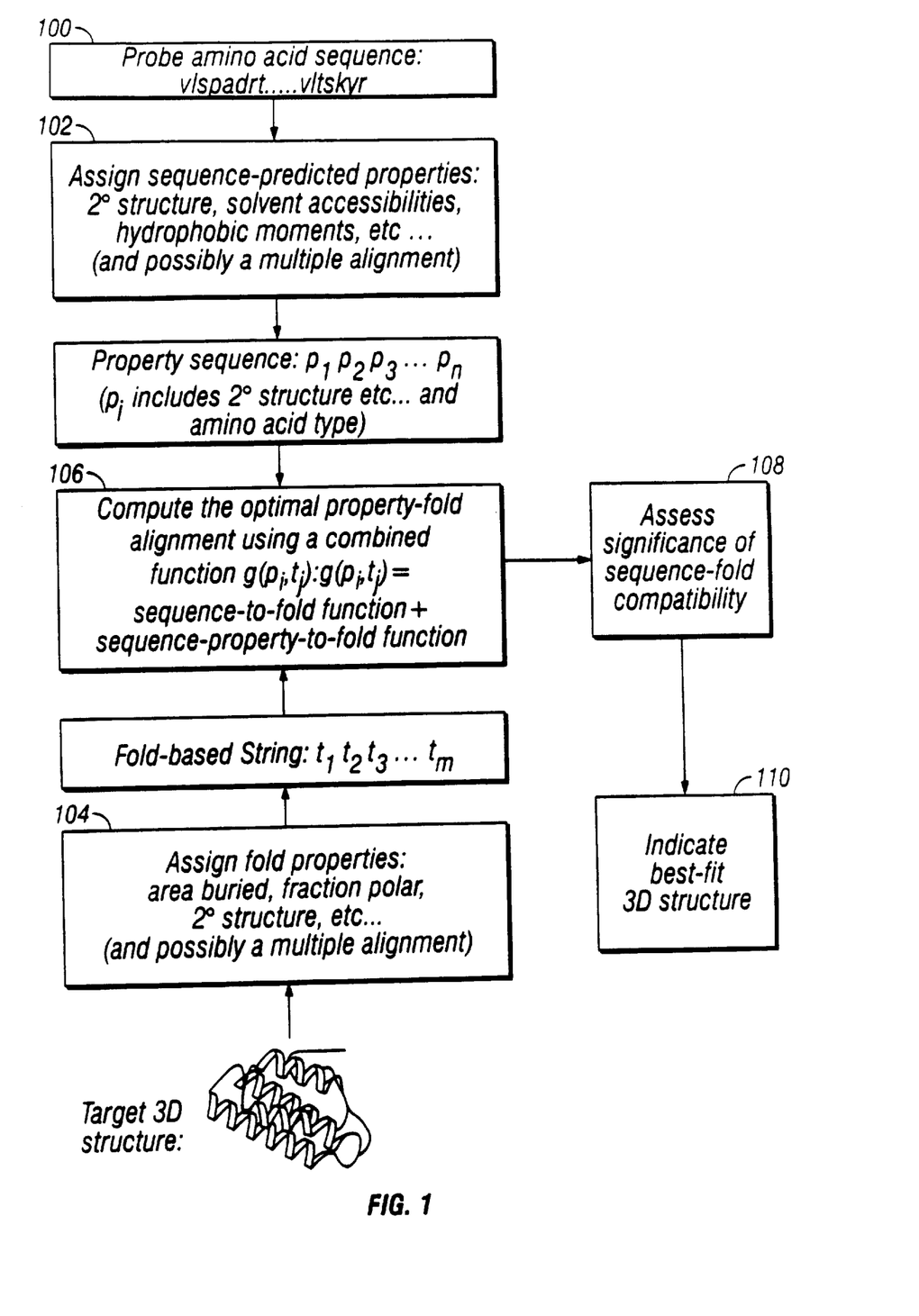
FIG. 1 is a flowchart showing the preferred embodiment of the invention.

FIG. 1 is a flowchart showing the preferred embodiment of the invention, which may be summarized as follows:

STEP 100: The amino acid sequence of a probe sequence is input into a programmed computer.

STEP 102: Using the amino acid sequence of the probe sequence, a number of sequence-derived properties are predicted by applying known algorithms using the computer, or simply retrieved from a database of pre-computed values (i.e., a "lookup table"). These properties may include one or more of the secondary (2°) structure, solvent accessibility, and hydrophobic moments of the probe sequence. If there are any similar sequences in the sequence database, a multiple alignment can be computed and used as one of the sequence-derived properties. The amino acid sequence is thus converted to a string $p_1, p_2 \ldots p_n$ of properties. Alternatively, the string of properties $p_1, p_2 \ldots p_n$ may be manually determined and input into the computer.

STEP 104: For each member of a library of known 3D structures, a string $t_1, t_2 \ldots t_m$ of structural properties is computed and stored in the computer (e.g., by applying the technique taught in Bowie et al., supra). Alternatively, the string of structural properties $t_1, t_2 \ldots t_m$ may be manually determined and input into the computer.

STEP 106: An alignment algorithm executing in the computer computes a score indicating the optimal alignment of the string $p_1, p_2 \ldots p_n$ to each string $t_1, t_2 \ldots t_m$ by applying a combined compatibility function $g(p_i, t_j)$= sequence-to-fold function+sequence properties-to-fold function.

STEP 108: The significance of the sequence-fold compatibility is assessed by ranking the scores and computing their statistical significance (e.g., by computing a z-score) to determine a best-fit (highest ranking) alignment score.

STEP 110: The best-fit alignment score is taken as a prediction of the correct assignment of the probe sequence to the corresponding known 3D protein fold structure, and may be used to indicate or select the 3D structure from the library for output to a user. The selected 3D structure may also be displayed (e.g., on a visual display device), although the selected 3D structure may differ in some ways from the actual structure of the probe sequence because of gaps and because of the differences in sequence. The secondary structure of the selected 3D structure and its actual amino acid sequence output may also be output.

Combined Compatibility Functions

This invention makes use of various combined compatibility functions $g(p_i, t_j)$, that include various previously derived functions as well as sequence-derived properties. The new compatibility functions, $g(p_i, t_j)$, relate information at position i of a probe sequence with position j of a target structure, and are composed of two parts. One component of g, termed f, uses any of several known probe sequence-target fold compatibility functions (i.e., functions that consider only the amino acid type at position $p_i$ of the probe). The second component of g, termed h, considers one or more sequence-derived properties of $p_i$. Thus, the inventive method uses both the sequence of the probe (the function) and its predicted sequence-derived property (the h function) to score the probe-to-target compatibility.

One simplified compatibility function g is defined as follows:

$$g(p_i, t_j) = f(aa_{p_i}, t_j) + w \times h(p_i, t_j) \quad (1)$$

A generalization of Equation 1 is defined as follows:

$$g(p_i, t_j) = w' \times \sum_{k=1}^{20} ma_{p_i}[k] f(k, t_j) + w \times h(p_i, t_j) \quad (2)$$

In both cases, the terms are defined as follows.

(1) The probe sequence. A probe sequence P of length n is represented as a string $p_1, p_2 \ldots p_n$. $p_i$ refers to some predicted structural property(ies) of the ith amino acid (residue) of a probe sequence. For example, $p_i$ can include any of the following information about residue i of P:

Amino acid type, denoted as $aa_{p_i}$.

Predicted secondary structure and its reliability value, denoted as $ss_{p_i}$ and $relss_{p_i}$, respectively.

Predicted solvent accessibility and its reliability value.

A weights vector of size 20, containing the composition of the amino acid types aligned at $p_i$ in a multiple alignment, denoted as $ma_{p_i}$. $ma_{p_i}[k]$ denotes the weight assigned to amino acid of type k in $p_i$.

The predicted secondary structure and solvent accessibility (and the corresponding reliability values) are available, for example, from the PHD server (Rost & Sander, "Prediction of protein secondary structure at better than 70% accuracy", *J Mol Biol* 232: 584–599 (1993)).

Any other desired information that can be assigned to each $p_i$ may also be included. For example only, a single specific sequence-derived property, predicted secondary structure, will he used in general to illustrate application of the invention.

(2) The target structures. Each target structure T of length m is represented as a string $t_1, t_2 \ldots t_m$. $t_j$ refers to some known structural property(ies) of the jth amino acid of in the target structure. The invention defines new compatibility functions that relate each position $p_i$ of a probe sequence P to a structural position $t_j$ of a fold T. These functions combine previously derived sequence-to-structure compatibility functions (which consider only the amino acid sequence of the probe) with the predicted structural; information at each $p_i$. Thus, the particular representation of the structures is the same as the ones required by the previously developed compatibility functions (see below). These may include the local secondary structure, $ss_{t_j}$, the amino acid type, denoted as $aa_{t_j}$, or the solvent accessibility and/or polarity of the residue at position j of structure T.

In addition to $aa_{t_j}$, a multiple alignment of sequences related to T can also be included as a weights vector, denoted as $ma_{t_j}$, in a similar way to $ma_{p_i}$, described above for the probe sequence.

(3) The function f. The function $f(aa_{p_i}, t_j)$ is a compatibility function relating the probe sequence to target, and only considers the amino acid types at $p_i$. Examples of such functions include the 3D-1D scores of Bowie et al., supra, or a substitution matrix such as that of (1) Dayhoff et al., "A model of evolutionary change in proteins" in Dayhoff M O, ed., *Atlas of Protein sequence and Structure*, vol. 5, suppl. 3. Washington, D.C.: National Biomedical Research Foundation. pp 345 (1978) or (2) Gonnet et al., "Exhaustive matching of the entire protein sequence database", *Science* 256: 1433–1445 (1992). In Equation 2, the sum goes over each of the 20 natural amino acid types k.

TABLE 2 below lists several examples of f functions that have been used in embodiments of the invention. However, f can be a more elaborated compatibility function. For example, Yi and Lander, in "Recognition of related proteins by iterative template refinement (ITR)", *Protein Sci* 3: 1315–1328 (1994), propose a compatibility function that combines sequence and structure information from the target:

$$f(k, t_j) = w_l \sum_{l=1}^{20} ma_{p_j}[l] f_l(k, l) + w_2 f_2(k, t_j) \quad (3)$$

where $f_1$ relates the amino acid type k of the probe sequence to the amino acids in the multiple alignment at position j of T (using a sequence-sequence substitution table), and $f_2$ is a sequence-to-structure compatibility function (such as the 3D-1D scores of Bowie et al., supra).

TABLE 2

Previously derived sequence-to-fold compatibility functions used to build new, combined sequence-derived properties-to-fold compatibility functions*

| Symbol | $f(aa_{pi}, t_j) =$ | Description |
| --- | --- | --- |
| 0 | 0 | Alt 0's |
| how | Sequence to environment | 3D-1D scores (Bowie, et al., 1991) |
| id | 1 if $aa_{pi} = aa_{tj}$, 0 otherwise | Identify matrix |
| blo | Blosum62 matrix | Blocks of aligned motifs (Henikoff & Henikoff, "Amino acid substitution matrices from protein blocks", Proc Natl Acad Sci USA 89: 10915–10919 (1992)) |
| gon | Gonnet matrix | Substitutions from database alignments (Gonnet, et al., "Exhaustive matching of the entire protein sequence database", Science 256: 1433–1445 (1992)) |

*The "symbol" column refers to the name used in this description. These functions are combined with the h functions defined in the text to create the new compatibility functions. For example, $g_{blo}$ refers to the new combined g function using as f the Blosum62 matrix (see text). The function "0" ignores the amino acid sequences of the probe and the target (the compatibility is measured exclusively by the function h). The latter is useful to quantify the amount of information contained in the prediction.

(4) The function h. The function $h(p_i, t_j)$ is the extended compatibility function that relates sequence-derived properties to the target structure. In one embodiment, $h(p_i, t_j)$ is simply defined as: $h(p_i, t_j) = v * relss_{p_i}$, where v is 1 if $ss_{p_i}$ is equal to $ss_{t_j}$ (if position i in the probe sequence has the same predicted secondary structure as position j in the known 3D structure), and −1 otherwise. h can also be extended to include other properties, such as the solvent accessibility, polarity, or the hydrophobic moment.

(5) The constants w' and w. w' and w are empirically determined weights. Determining the optimal values for w is not trivial. The value of w is determined based on the following idea: if the predicted structure of $p_i$ is the same as the actual structure of $t_j$, then we would like to reflect this by increasing the compatibility value of this match, thus encouraging the match of this pair during the alignment algorithm. Conversely, if the predicted structure differs from the actual structure, we would like to have a lower compatibility value for this match, thus encouraging an insertion or deletion in the alignment.

Thus, the actual optimal value of w is somewhat related to the value of adding a gap in the alignment. For simplicity, we choose w to be equal to the gap extension penalty used in the alignment algorithm. The performance of any compatibility function depends critically on the values of the gap penalties (see below). Choosing w to be equal to the gap penalty extension does not require a separate optimization for this parameter. However, alternative values for w, which are independent of the value of the gap extension penalty, may produce better results.

Thus, in one embodiment of the invention, the combined compatibility function simply adds (or subtracts) the product of the gap penalty value (w) and h (in this case, determined by $relss_{pi}$) to (or from) the compatibility value given by f, depending on the similarity between the predicted and actual structures.

Alignment Algorithm

In the preferred embodiment of the invention, the optimal alignment between the derived properties of a probe sequence and the structural properties of a target is carried out using a dynamic programming algorithm. Dynamic programming algorithms are taught in Needleman & Wunsch, *J. Mol. Biol.,* 48, 443–453 (1970) and Smith & Waterman, *Adv. Appl. Math.,* 2, 482–489 (1981), and their use is discussed and demonstrated in Gribskov et al., *Proc. Natl. Acad. Sci. U.S.A.,* 84, 4355 (1987); Gribskov et al., *CABIOS* 4, (1988); Gribskov & Eisenberg, in "Techniques in Protein Chemistry" (T. E. Hugli, ed.), p. 108. Academic Press, San Diego, Calif., 1989; Gribskov et al., *Meth. in Enz.* 183, 146 (1990) (all incorporated herein by reference). Any comparable search technique could also be used.

More particularly, there are two common variations of the dynamic programming algorithm: The "local" algorithm finds the highest-scoring aligned segment, allowing unpenalized-unaligned N- and C-termini both in the sequence and in the structure. The "global" alignment algorithm allows at most two unaligned termini without penalization, but requires that at least one N-terminus segment and one C-terminus segment of either the sequence or the structure be either aligned or penalized. The preferred embodiment uses a different variation, dubbed the "global-local" alignment. This algorithm does not penalize unmatched N- or C-termini segments in the probe sequence (local alignment), but does penalize any gaps in the target structure (global alignment). This variation produces more reliable scores than those obtained by the commonly used global or local algorithms. See Fischer et al., "Assessing the performance of inverted protein folding methods by means of an extensive benchmark", *Proc 1st Pacific Symposium on Biocomputing:* 300–318, http://www.pharm.ucsf.edu/psb/psb96/proceedings/eproceedings.html (1996).

Dynamic programming algorithms require that the user specify the values of the gap penalties to be applied. Usually, gap penalties are specified as a gap opening penalty (O) and a gap extension penalty (E). The overall penalty for a gap in the alignment is given by O+nE, where n is the length of the gap. There is no single set of values that is best for different methods. Even for different sequences, the optimal gap penalties vary. In the preferably embodiment, gap penalties are optimized for each compatibility function separately. Because there is no known analytic method to calculate optimal penalties, the approach taken here is a brute-force search method (see Fischer et al., supra): for each evaluated compatibility function, a range of gap penalties was tested using the benchmark's probe sequences and a reduced library of folds (see below). The best combination of O and E was then used with the full-size library.

Ranking and Significance Estimation

The global-local alignment algorithm allows the use of the raw scores of the alignments to rank the results, without any normalization. When the sequence-derived properties of a probe sequence are compared to all the known 3D target folds in a library, a list of scores is generated, indicating the compatibility of each target fold to the probe sequence. There will always be a rank-1 fold. This does not necessarily imply that the probe sequence has such a fold. To be able to determine how significant this rank-1 fold is (or in other words, how likely or unlikely it is that this match arises by chance), in the preferred embodiment, a z-score (the number of standard deviations above the mean score) is computed from a given distribution (see Fischer et al., supra). In the present example, the distribution was computed by optimally aligning a number of randomly permuted sequences drawn from the probe sequence, and is denoted Z* in TABLE 4 below. From tests on known probe-target pairs, a Z* score above 7 has always been a true positive (results not shown).

Validation of Sequence-derived Properties

The performance of various combined functions g were evaluated using different previously derived functions f (see Equation 1 and TABLE 2). For example only, a single specific sequence-derived property, predicted secondary structure, was used in determining h, to illustrate application of the invention.

For each choice of function f, three comparisons were performed. The first comparison corresponds to functions using the previously derived compatibility functions alone, without considering the predicted secondary structure (i.e., w=0 in Equation 1). We denote this type of comparison as $g_x^s$, s denoting that only the sequence of the probe is used. The subscript x indicates the type of previously derived compatibility function f applied, as shown in TABLE 2 (i.e., x is id, blo, gon, bow, or 0). The second comparison is with the new combined compatibility functions, using the predicted secondary structure (i.e., w>0). We denote this type of comparison as $g_x^p$, p denoting that the predicted information is used. The third comparison is also with the new combined compatibility functions, but, instead of using the sequence-derived predictions, the actual secondary structures of the probe sequences are used. We denote this type of comparison as $g_x^r$, r denoting that the real structural information is used. This real information is obtained from the structures of the probe sequences, which are actually known. The $g^s$ and $g^r$ functions are used here to determine the expected lower and upper bounds for the performance of the $g^p$ functions. This three-way comparison allows us to determine whether the use of the predicted information increases performance and whether a more accurate prediction will be even better.

Each of the compatibility functions described above was evaluated using a benchmark that assesses the performance of any fold-recognition method (Fischer et al., supra). The benchmark allows for a systematic evaluation of the relative merits of each component of a fold-recognition method.

Here, only the compatibility function is tested; the other components are left unchanged.

The benchmark consists of a library of 301 known target structures and a set of 68 probe sequences that cover a wide range of structural classes and folds. The most compatible target fold for each probe sequence is unknown to the method being tested, but is known to the benchmark and is pre-computed by structural comparison (see Fischer et al., supra, for details). The sequence identity between the probe sequence and the sequence of the target fold is below 30% for all pairs. For each of the 68 probe sequences, the evaluated method performs a computer scan of the library of known folds and produces a ranked list of compatibilities. The benchmark registers at what rank the "expected" fold of each probe sequence is found. The number of correct folds that are identified at rank 1, at better than rank 5, and at better than rank 10, are computed. In addition, for this example, the overall performance score of a method is computed as $S^*=\{\Sigma(1/r_i)\}/68$, where the sum is taken over all probes, $r_i$ denotes the rank of the correct fold achieved by probe i, and 68 is the number of probes in the benchmark. $S^*$ equals 1.0 for perfect fold assignment (and <0.01 for random assignment).

Figure 2A:
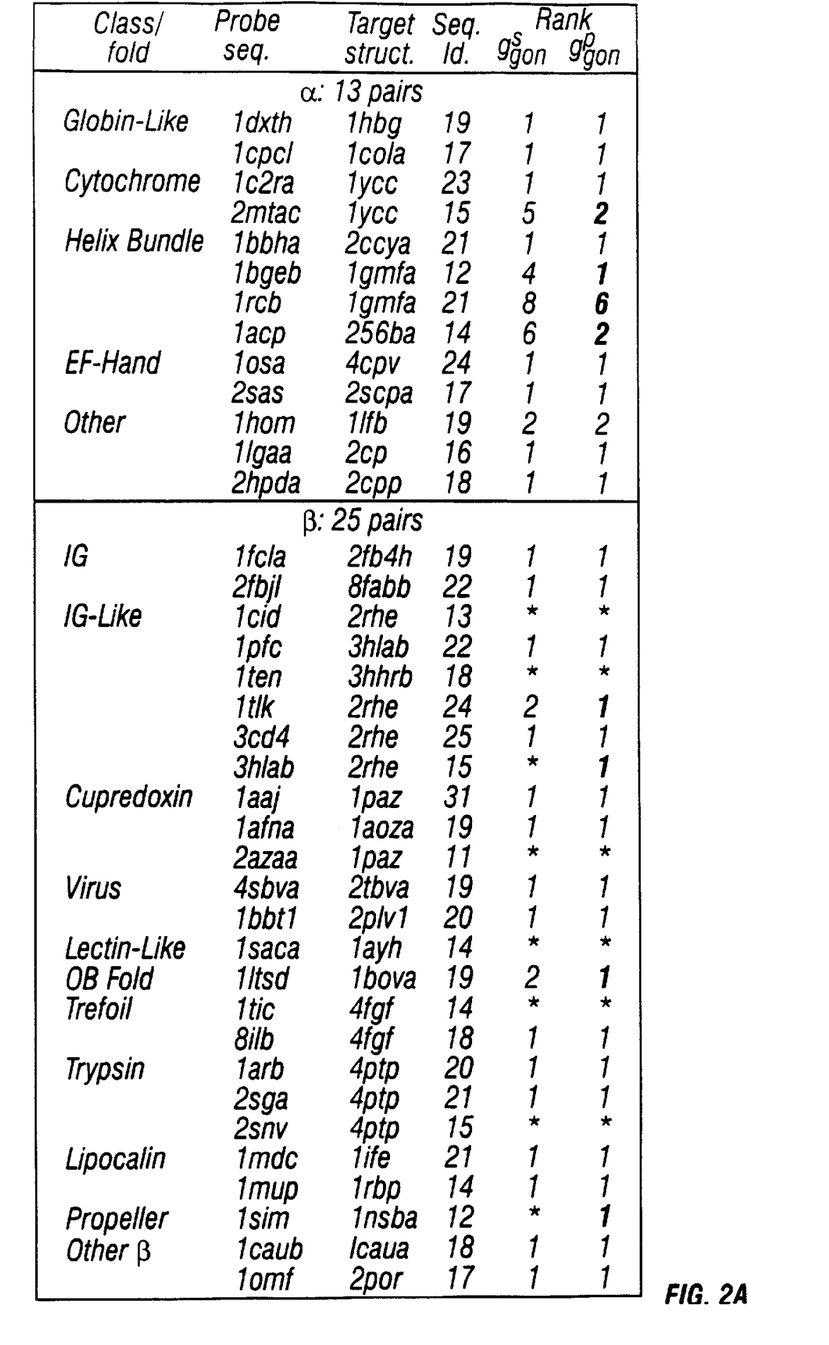
FIG. 2A and FIG. 2B list the 68 probe-target pairs, along with their sequence identity percentage, of the benchmark applied to evaluate several embodiments of the invention.
Figure 2B:
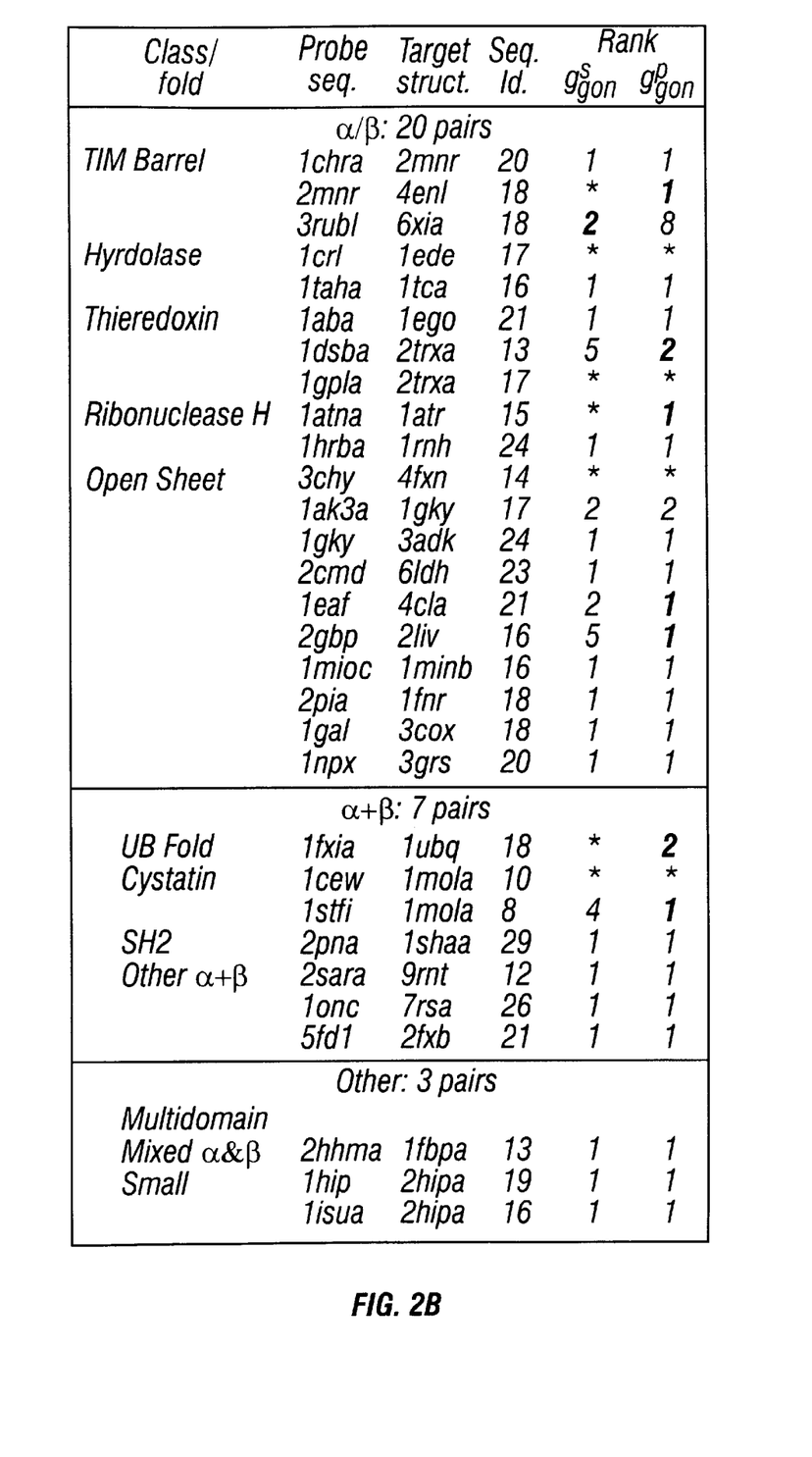

FIG. 2A and FIG. 2B list the 68 probe-target pairs, along with their sequence identity percentage, of the benchmark applied to evaluate these embodiments of the invention. Each sequence-fold pair is listed according to its structural class and type of fold. The sequence identity percentage between probe and target is indicated, as computed by the GAP program (from Genetics Computer Group) with default parameters. Note that the sequence identity computed from the actual structural superposition will, in general, produce much lower values. The "RANK" column shows the rank the expected target obtained when scanning the fold library using the probe sequence. Two numbers are shown. The one under the column labeled "$g_{gon}{}^s$" corresponds to the rank obtained using the Gonnet sequence-sequence substitution matrix alone. The one under the column labeled "$g_{gon}{}^p$" corresponds to the rank obtained using a combined compatibility function in accordance with one embodiment of the invention (i.e., combining the Gonnet table with the predicted secondary structure). The lowest of the two numbers is shown in bold. In all cases except one, the $g_{gon}{}^p$ compatibility function performed better or equal than the $g_{gon}{}^s$ function. An asterisk indicates the rank is above 10. (This figure was adapted from Fischer et al., supra.)

TABLE 3 summarizes the results of the three-way comparison on each of the compatibility functions f used. The first column gives the symbol of the compatibility function used as described in TABLE 2. The second column describes the optimal gap opening (O) and gap extension (E) penalties as obtained by the brute-force method described above. The next three numbers indicate the number of test probes that identified their target structure in ranks <10, <5, and =1. Total numbers of probes is 68. Overall score S* is computed as $\{\Sigma(1/r_i)\}/68$, where $r_i$ is the rank at which the expected fold of probe i is found. A perfect sensitivity would be: 68, 68,68, with an overall score of 1.00.

TABLE 3

Sensitivity in fold assignment of various compatibility functions (g)

| Compatibility function | | Gap Penalty | | In rank | | | Overall |
|---|---|---|---|---|---|---|---|
| Secondary structure | Symbol | O | E | <10 | <5 | 1 | score S* |
| $g_o$: Secondary structure only (no sequence) | | | | | | | |
| Predicted | $g_o{}^p$ | 0.0 | 0.70 | 47 | 38 | 26 | 0.48 |
| True | $g_o{}^r$ | 0.0 | 0.70 | 53 | 43 | 34 | 0.58 |
| $g_{how}$: 3D-ID scores | | | | | | | |
| None | $g_{id}{}^s$ | 1.8 | 0.20 | 43 | 35 | 25 | 0.46 |
| Predicted | $g_{id}{}^p$ | 1.8 | 0.20 | 48 | 42 | 31 | 0.56 |
| True | $g_{id}{}^r$ | 1.8 | 0.20 | 51 | 49 | 38 | 0.64 |
| $g_{ic}$: Identify matrix | | | | | | | |
| None | $g_{id}{}^s$ | 1.4 | 0.15 | 43 | 40 | 29 | 0.50 |
| Predicted | $g_{id}{}^p$ | 1.4 | 0.15 | 50 | 45 | 37 | 0.61 |
| True | $g_{id}{}^r$ | 0.8 | 0.37 | 54 | 53 | 49 | 0.76 |
| $g_{blo}$: Blosum matrix | | | | | | | |
| None | $g_{blo}{}^s$ | 5.2 | 1.00 | 52 | 45 | 37 | 0.61 |
| Predicted | $g_{blo}{}^p$ | 5.2 | 1.00 | 55 | 49 | 44 | 0.70 |
| True | $g_{blo}{}^r$ | 4.0 | 2.36 | 60 | 57 | 50 | 0.78 |
| $g_{gon}$: Gonnet matrix | | | | | | | |
| None | $g_{gon}{}^s$ | 10.8 | 0.60 | 51 | 50 | 40 | 0.66 |
| Predicted | $g_{gon}{}^p$ | 10.8 | 0.60 | 58 | 56 | 48 | 0.77 |
| True | $g_{gon}{}^r$ | 10.8 | 1.92 | 60 | 58 | 52 | 0.80 |

For each function f, three evaluations are shown: $g^s$, $g^p$, and $g^r$, representing the results of the benchmark: (1) ignoring the secondary structure prediction, (2) using the prediction, and (3) using the actual secondary structure, respectively. (Notice that $g_o{}^s$ is not shown, because this function is not applicable.) For each f, the $g^p$ functions performed better than the $g^s$ functions and worse than the $g^r$ functions. This means that predicted secondary structure always improves the scores, and that perfect secondary structure prediction would improve the scores even more. It is interesting to note that, although the gap penalties were optimized separately for each function (see discussion above), the optimal values obtained for $g^p$ and $g^s$ are the same.

Figure 3:
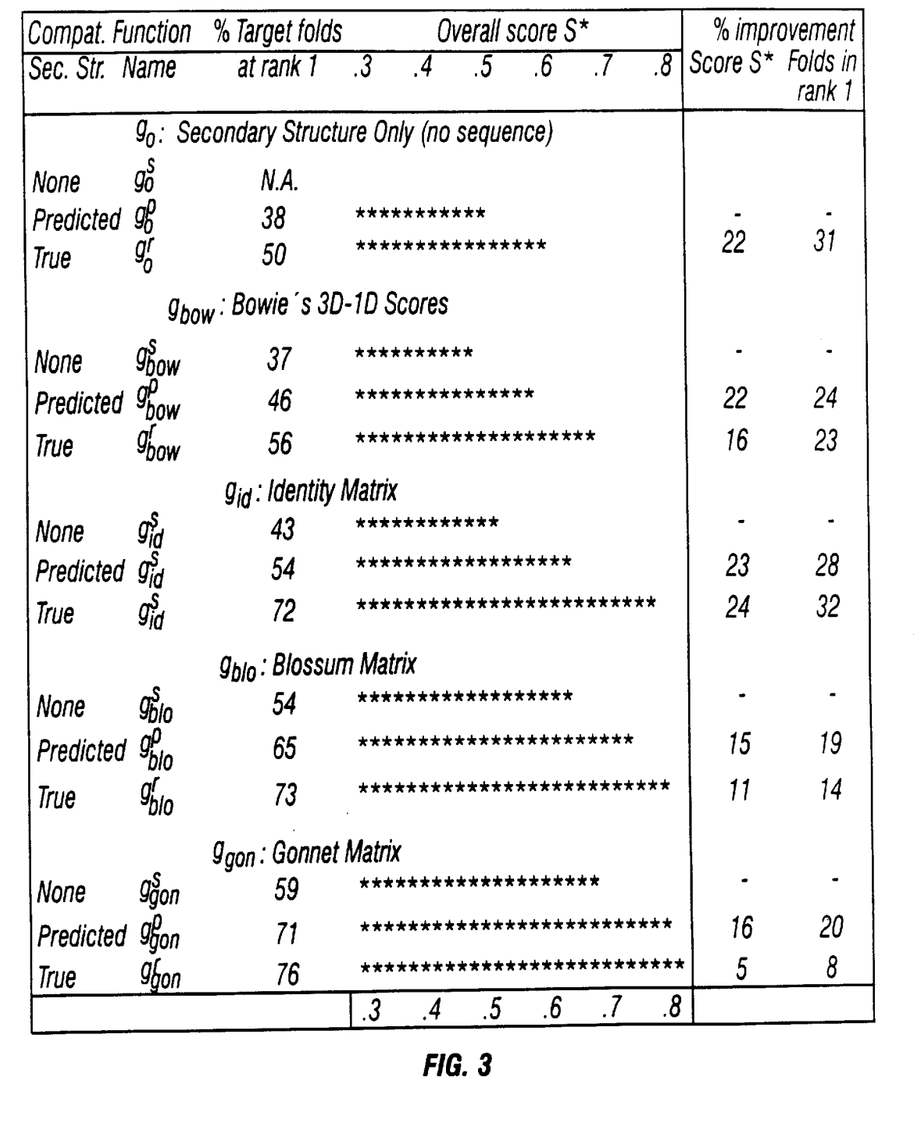
FIG. 3 graphs the overall score S* of each compatibility function in accordance with the example embodiment.
Figure 4A:
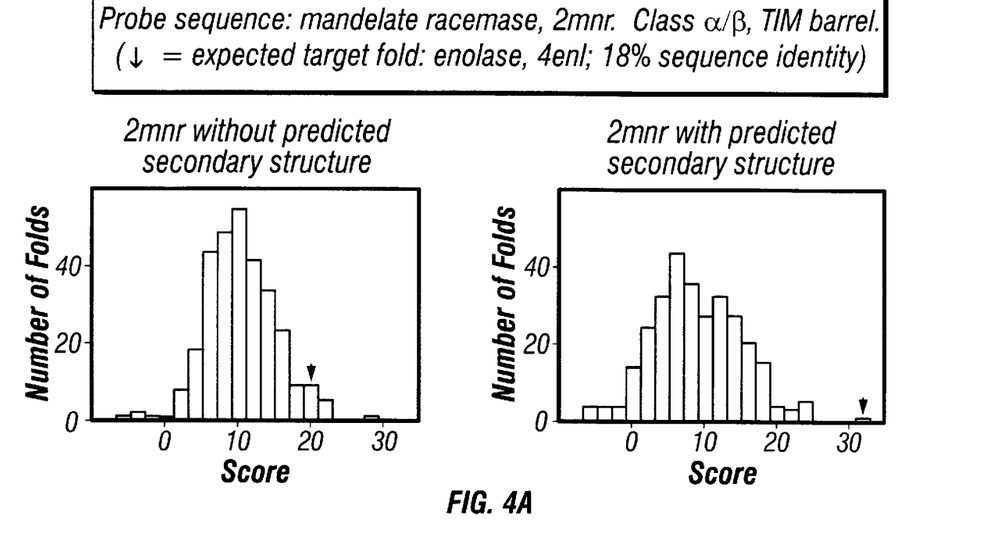
FIGS. 4A–4E are graphs of probe sequence to fold assignments, showing that considering the sequence-derived property of predicted secondary structure improves fold assignment.
Figure 4B:
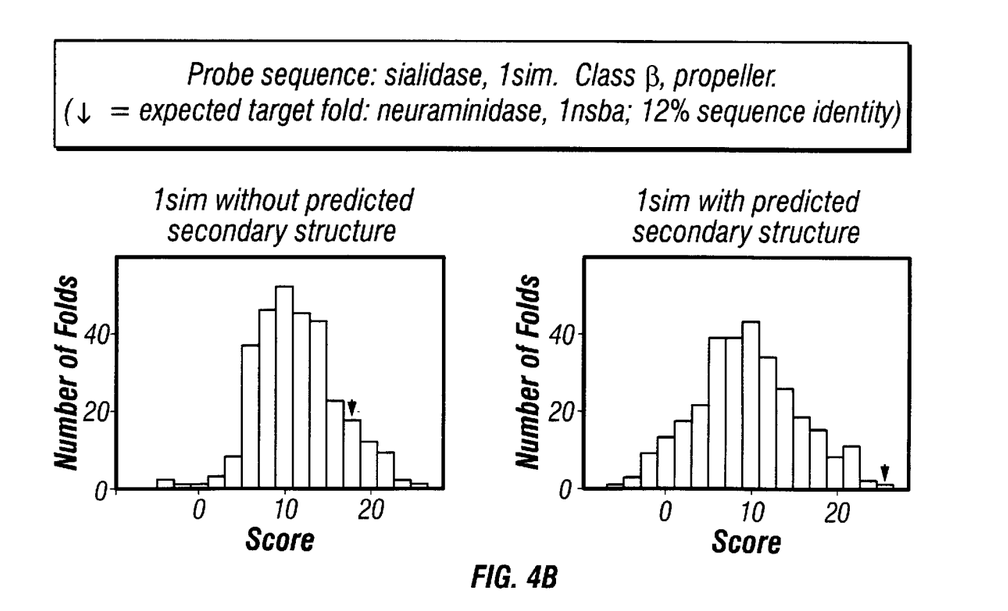
Figure 4C:
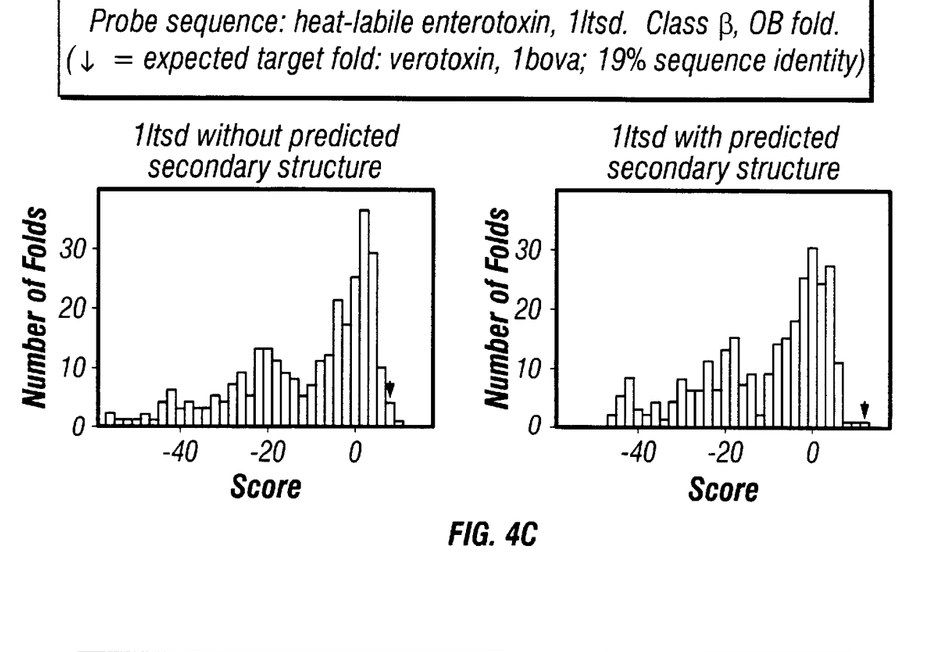
Figure 4D:
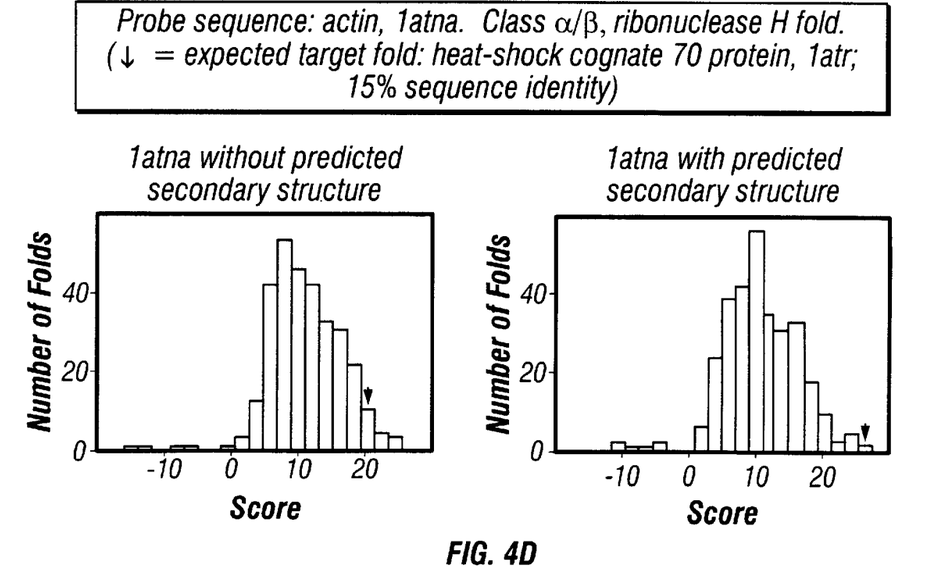
Figure 4E:
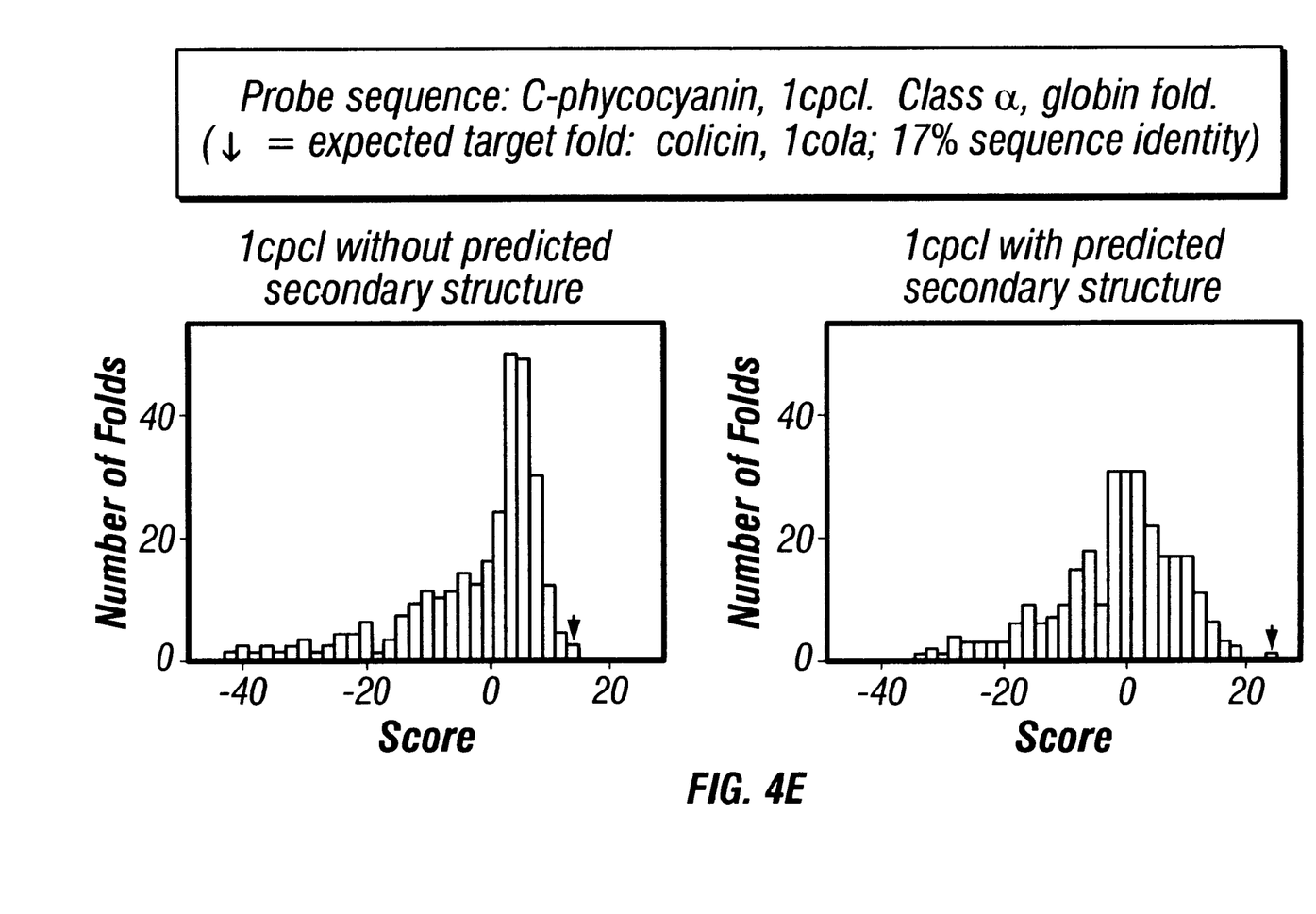

FIG. 3 graphs the overall score S* of each compatibility function in accordance with the example embodiment. The graph shows for each of the g compatibility functions evaluated: the percentage of probe sequences (out of 68) that identified the correct target fold in rank one, the overall score of the method as assessed by the benchmark (S*), and, on the far right, the percentage improvement obtained when using the predicted or experimentally determined secondary structure of the probe. The percentage of improvement is computed using either the overall score or the number of probes that identify the correct fold at rank one. For $g^p$, the increase in percentage over $g^s$ is shown, and for $g^r$, the increase over $g^p$ is indicated. The increase in performance of $g^p$ over $g^s$ ranges between 15 and 22% for the overall score and between 19 and 28% for the number of correctly identified folds. The increase in performance of $g^r$ over $g^p$ ranges between 5 and 24% for the overall score and between 8 and 32% for the number of correctly identified folds. Notice that the largest improvements occur for the less sensitive compatibility functions (above 23% for the less sensitive id and bow matrices, 14% for blo, and only 8% for gon). The results also show that for the id, blo, and gon functions, the $g^r$ results are very similar one to another, i.e., the difference between the identity (id) and the Gonnet (gon) tables using the real structures is minimal. Also notice that, in all cases, the performance of the functions f is: gon>blo>id>bow>0.

Selected Examples

To demonstrate some of the recognition problems that the inventive method is able to solve, we selected five probe sequences from the benchmark (see FIG. 2A and FIG. 2B). For these five sequences, $g_{gon}^P$ identified the correct fold in rank one, whereas $g_{gon}^s$ placed only one in rank one. The five probe sequence-target fold pairs are the heat-shock-actin proteins, colicin-phycocyanin, having the globin fold, two TIM barrels, two OB folds, and two propeller folds.

For each of the five examples, FIGS. 4A–4E are graphs of probe sequence to fold assignments, showing that considering the $g_{gon}^P$ compatibility function. Six fold assignments are given that are not detectable by standard sequence-sequence comparison methods; for two of these, the fold is known from X-ray crystallography and the fold assignment made by the inventive method is correct. For each of the six probe sequences, the fold achieving the best score is listed in TABLE 4, along with the Z*-score associated with the match.

TABLE 4

Assignment of six probe sequences to known target folds for cases in which sequence comparison methods fail

| | Probe Sequence | | | Target Structure | | | Compatibility | |
|---|---|---|---|---|---|---|---|---|
| SW code | aa | P(1) | Description | PDB code/fold | aa | Description | 1d%/1a | Z* |
| atty_human | 454 | NF | Tyrosine amino-transferase | 7aata α/β: PLP transf. | 401 | Aspartate amino-transferase | 17% 386 | 6.7 |
| amic_pseae | 384 | C | Aliphatic amidase-regulator protein | 2liv α/β: Periplasmic | 354 | LEU/ISO/VAL binding protein | 18% 337 | 13.6 |
| arfl_arath | 180 | NC | ADP-ribosylation factor 1 | 5p21 α/β: Rossmann | 166 | Ras p21 protein | 19% 161 | 9.1 |
| nidm_bovin | 175 | | NADH-ubiquinone oxidoreductase | 1hmca α: Helix bundle | 148 | Macrophage col. stim. factor | 19% 132 | 5.9 |
| yeil_ecoli | 219 | | Hypothetical 25.3 KD protein | 3gapa 2lMixed | 208 | Catabolite gene activator | 18% 189 | 10.0 |
| ggpp_sulac | 330 | F | Geranylgeranyl pyrophos.syntase | 1fps α: Multihelical | 348 | Farnesyl diphosph. syntase | 25% 319 | 10.9 | ering the sequence-derived property of predicted secondary structure improves fold assignment. For each probe sequence, the distribution of scores obtained when computer scanning the benchmark's library of 301 folds is shown. The distributions show the number of folds in the library at each score range. For each probe sequence, two histograms are shown. One corresponds to the results using the sequence-only $g_{gon}^s$ function, and the other corresponds to the results using the combined $g_{gon}^P$ compatibility function. For clarity, the low-score tails of some histograms are not shown. The score of the expected fold is indicated with an arrow. The Protein Data Bank (PDB; see Bernstein et al., "The Protein Data Bank: A computer-based archival file for macromolecular structures", *J Mol Biol* 112: 535–542 (1977)) codes and names of the probe sequence and target folds are indicated. The class (α, β, α/β, or α+β), the type of fold, and the sequence identity between probe and target are also shown.

In each case, the combined function not only identifies the expected fold at rank one, but also discriminates better between the actual fold and other folds. For example, with the $g_{gon}^s$ function, using actin (1atna) as a probe, the heat-shock protein (1atr) ranks 15 with a score of 20. The 14 proteins above it are false positives. With the $g_{gon}^P$ function, 1atr ranks 1 with a score of 26.

As another test, the method of the invention was used to assign folds to probe sequences from the SWISSPROT database (Bairoch & Boeckmann, "The SWISSPROT protein sequence data bank", *Nucleic Acids Res* 20: 2019–2022 (1992)). More particularly, to apply the inventive method of sequence-derived predictions to probe sequences outside of our benchmark sequences, we searched a representative set of the SWISSPROT database for those probe sequences that can be assigned to known folds. For the SWISSPROT searches, we used an updated library derived from the PDB, which contains the structures of about 800 chains. TABLE 4 lists six sequence-fold assignments made in this way using In TABLE 4, column P indicates whether the similarity has been detected prior to this work: C means a crystal structure exists for the probe (the structure of amic_pseae was not available, but the similarity to 2liv has been reported); F means the probe is known to have a similar function or belong to a similar family; N means the compatibility has been noted by previous authors. To our knowledge, the other fold assignments have not been noted before. Id% and la indicate the sequence identify percentage and the length of the alignment of the probe and target, respectively. Z* refers to the Z*-score obtained for the pair, as described above.

Members of these sequence-fold pairs share less than 25% sequence identity. As a point of contrast, sequence comparison methods (the FASTA program, Pearson & Lipman, "Improved tools for biological sequence comparison", *Proc Natl Acad Sci USA* 85: 2444–2448 (1988), and the BLAST program, Altschul et al., "Basic Local Alignment Tool", *J Mol Biol* 215: 403–410 (1990)) obtain low scores for these pairs, and proper targets are not unambiguously identified by these two programs.

We noted three additional fold assignments that obtained quite high Z* scores (>10). Even though the sequence identity between probe and target for these pairs is not significant (<25%), these three assignments are not included in TABLE 4 because they may be identifiable with classic sequence-sequence comparison methods (BLAST scores close to the 0.05 confidence threshold). These are: SPHX protein precursor with phosphate-binding protein, BLAST score of 0.066; renilla-luciferin 2-monooxygenase with haloalkane dehalogenase, BLAST score of 0.002; and coat protein from nicotianan velutina M.V. with tobacco mosaic virus, BLAST score of 0.08.

TABLE 4 suggests that the method of sequence-derived predicted properties is capable of detecting significant compatibility of probe sequences of unknown structure to target 3D structures, when other sequence comparison methods fail. In three of the examples, compatibility has been suggested earlier by other workers, supporting the correctness of our assignments.

Advantages

The fold-recognition method of the invention uses information from sequence-derived properties. This is done with combined compatibility functions which, depending on the similarity between the predicted and actual secondary structures, add (or subtract) the product of the gap penalty value (w) and the reliability of the prediction to (from) the compatibility value given by a previously derived compatibility function. In particular, inclusion of secondary structure prediction is of definite benefit in fold recognition—not only do the $g^p$ functions perform better than the $g^s$ functions, but also they separate better the correct folds from the incorrect ones (see FIGS. 4A–4E). Using only predicted secondary structure ($g_0^p$), 38% of the probe sequences identified (were assigned to) their correct structure. Using the Gonnet matrix alone ($g_{gon}^s$), 59% of the probe sequences identified their correct structure, whereas in the combined method ($g_{gon}^p$), this number increased to 71%. A similar improvement was observed for the other compatibility functions evaluated.

Further, the inventive method is robust when incorrect predictions are used. The reliability of the prediction is taken into account by adding a constant proportional to the value of the predicted reliability. Thus, with a less reliable prediction, the actual value of $g(p_i, t_j)$ will be mostly determined by $f(p_i, t_j)$. In a number of cases using probe sequences with less reliable predictions (results not shown), if the predicted reliability value were ignored (i.e., $h(p_i, t_j)$ is 1 or −1), we observed a slight reduction in performance. In the benchmark test described above, most probes had more than one homologue in the database, so multiple alignments could be used in the prediction, probably giving better accuracies in the secondary structure prediction. When a probe sequence has no homologues, the prediction may be less accurate and weighting according to the predicted reliability is of greater importance.

More accurate secondary structure predictions would improve the performance of the inventive fold-recognition method, since perfect predictions improve performance (in all cases shown above, $g^r > g^p$, meaning that reality beats prediction).

The inventive method can be extended to include the information in the multiple alignment of both the probe sequence ($ma_{pi}$) and the target structures ($ma_{tj}$), as well as including other predicted properties such as the solvent accessibility.

The results in this work do not suggest that we can expect to recognize the fold of a new probe sequence in 70% of the cases ($g_{gon}^p$ in FIG. 3). Using the particular set of probe sequences in the benchmark, we do succeed in 70% of the cases. However, one should take into account the following:

How similar is "structurally similar"? The 3D structures of the pairs in the benchmark were selected according to the following criterion: at least half the residues of the larger protein can be superimposed onto the smaller protein, each at a distance of, at most, 3 Å. There exist a number of known similarities between pairs of proteins that do not fulfill this criterion. There is no information on the performance of the methods evaluated here for such pairs. Thus, further evaluations using independently developed benchmarks would be of interest.

Sequence identity dependence. Of the 68 pairs in the benchmark, 3 pairs have a sequence identity above 25% and 16 have a sequence identity between 20 and 25%. Using the $g_{gon}^p$ compatibility function, the percentage of correctly identified pairs having above 20% sequence identity is 95, whereas the percentage for pairs below 20% is only 63. Thus, for probe sequences with higher sequence identity percentages (20–25%), the expected recognition accuracy is much higher. (The pairs above 20% sequence identity are nevertheless included in the benchmark because, although having relatively large sequence identity, they are not recognized by some of the fold-recognition methods we have evaluated. For comparison between methods, these pairs do not bias the results.) Thus, when a new probe is given, which has less than 20% sequence identity with any known structure, one should expect a recognition accuracy of about 63% rather than 70%.

Alignment accuracy or the "more luck than brains" artifact. It is well known in fold recognition that identifying the correct fold in a set of structures is a much easier problem than providing the correct alignment for a probe sequence and the fold. Using the combined compatibility functions of the invention, we observed an increase in the accuracy of the resulting alignments (results not shown). However, one should keep in mind that, due to the limited size of folds in the library, the length or composition similarities between probe sequence and target, or some other bias, it is possible to identify the correct fold in rank one, but the alignment can be useless for modeling a 3D fold for the probe sequence.

Computer Implementation

Aspects of the invention may be implemented in hardware or software, or a combination of both. However, preferably, the algorithms and processes of the invention are implemented in one or more computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM, CD-ROM, tape, or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, it will be understood that various modifications may be made without departing from the spirit and scope of the invention. Accordingly, other embodiments are within the scope of the following claims.

What is claimed is:

1. A computer-assisted method for assigning an amino acid probe sequence to a known three-dimensional protein structure, including the steps of:
   (a) receiving into a computer system a string describing the amino acid sequence of the probe sequence;
   (b) generating, from the amino acid string, at least one sequence-derived property for the amino acid sequence, defined as $p_1, p_2 \ldots p_n$, wherein each p represents the sequence-derived property of a corresponding amino acid of the probe sequence;

(c) inputting into the computer system a string $t_1, t_2 \ldots t_m$ of structural properties, wherein each t represents the structural property of a corresponding amino acid of the known three-dimensional protein, for each member of a library of known three-dimensional protein structures;

(d) executing an alignment algorithm in the computer system to compute an alignment score indicating the optimal alignment of the string $p_1, p_2 \ldots p_n$ to the string $t_1, t_2 \ldots t_m$ by applying a combined compatibility function $g(p_i, t_j)$;

(e) determining the statistical significance of each alignment score to determine a best-fit alignment score; and (f) applying the best-fit alignment score to indicate or select the corresponding three-dimensional protein structure from the library for output to a user.

2. The computer-assisted method of claim 1, wherein each string $t_1, t_2 \ldots t_m$ of structural properties is determined from a known one-dimensional and three-dimensional structure of a protein.

3. The computer-assisted method of claim 1, wherein the combined compatibility function $g(p_i, t_j)$ is of the form:

$$g(p_i,t_j)=f(aa_{p_i},t_j)+w \times h(p_i,t_j)$$

where $aa_{pi}$ is the amino acid type for $p_i$, w is a weighting factor, the function $f(aa_{pi}, t_j)$ is a compatibility function that relates the amino acid sequence of the probe sequence to structural properties of known three-dimensional protein structures, and the function $h(p_i, t_j)$ is an extended compatibility function that relates sequence-derived properties of the probe sequence to structural properties of known three-dimensional protein structures.

4. The computer-assisted method of claim 1, wherein the combined compatibility function $g(p_i, t_j)$ is of the form:

$$g(p_i, t_j) = w' \times \sum_{k=1}^{20} ma_{pi}[k] f(k, t_j) + w \times h(p_i, t_j)$$

where k is the amino acid type for $p_i$, w and w' are weighting factors, $ma_{pi}[k]$ denotes a weight assigned to amino acid of type k in $p_i$, the function $f(k,t_j)$ is a compatibility function that relates the amino acid sequence of the probe sequence to structural properties of known three-dimensional protein structures, and the function $h(p_i, t_j)$ is an extended compatibility function that relates sequence-derived properties of the probe sequence to structural properties of known three-dimensional protein structures.

5. The computer-assisted method of claim 1, wherein the alignment algorithm includes a dynamic programming algorithm.

6. The computer-assisted method of claim 5, wherein the dynamic programming algorithm includes a global-local alignment algorithm.

7. The computer-assisted method of claim 1, wherein the step of determining the statistical significance of each alignment score to determine a best-fit alignment score includes the step of computing a z-score as the number of standard deviations above a mean score.

8. The computer-assisted method of claim 1, wherein the step of applying the best-fit alignment score to indicate or select the corresponding three-dimensional protein structure from the library for output to a user includes the step of displaying the three-dimensional protein structure on a visual display device.

9. A computer-assisted method for predicting the three-dimensional structure of an amino acid probe sequence using a programmed computer comprising a processor, a data storage system, at least one input device, and at least one output device, including the steps of:

(a) generating input data for the programmed computer, including the steps of:

(1) determining a string $p_1, p_2 \ldots p_n$ describing the amino acid sequence of the probe sequence and at least one sequence-derived property for the probe sequence, wherein each p represents the sequence-derived property of a corresponding amino acid of the probe sequence;

(2) determining a string $t_1, t_2 \ldots t_m$ of structural properties, wherein each t represents the structural property of a corresponding amino acid of the known three-dimensional protein, for each member of a library of known three-dimensional protein structures;

(b) inputting the generated input data into the programmed computer through one of the input devices;

(c) applying, by means of the processor, an alignment algorithm to compute an alignment score indicating the optimal alignment of the string $p_1, p_2 \ldots p_n$ to the string $t_1, t_2 \ldots t_m$ by applying a combined compatibility function $g(p_i, t_j)$;

(d) determining the statistical significance of each alignment score to determine a best-fit alignment score;

(e) applying, using computer methods, the best-fit alignment score to identify the corresponding three-dimensional protein structure from the library; and (f) outputting to at least one output device the identity of such three-dimensional protein structure.

10. The computer-assisted method of claim 9, wherein the step of determining each string $t_1, t_2 \ldots t_m$ of structural properties includes the step of determining such structural properties from a known one-dimensional and three-dimensional structure of a protein.

11. The computer-assisted method of claim 9, wherein the combined compatibility function $g(p_i, t_j)$ is of the form:

$$g(p_i,t_j)=f(aa_{p_i},t_j)+w \times h(p_i,t_j)$$

where $aa_{pi}$ is the amino acid type for $p_i$, w is a weighting factor, the function $f(aa_{pi}, t_j)$ is a compatibility function that relates the amino acid sequence of the probe sequence to structural properties of known three-dimensional protein structures, and the function $h(p_i, t_j)$ is an extended compatibility function that relates sequence-derived properties of the probe sequence to structural properties of known three-dimensional protein structures.

12. The computer-assisted method of claim 9, wherein the combined compatibility function $g(p_i, t_j)$ is of the form:

$$g(p_i, t_j) = w' \times \sum_{k=1}^{20} ma_{pi}[k] f(k, t_j) + w \times h(p_i, t_j)$$

where k is the amino acid type for $p_i$, w and w' are weighting factors, $ma_{pi}[k]$ denotes a weight assigned to amino acid of type k in $p_i$, the function $f(k,t_j)$ is a compatibility function that relates the amino acid sequence of the probe sequence to structural properties of known three-dimensional protein structures, and the function $h(p_i, t_j)$ is an extended compatibility function that relates sequence-derived properties of the probe sequence to structural properties of known three-dimensional protein structures.

13. The computer-assisted method of claim 9, wherein the alignment algorithm includes a dynamic programming algorithm.

14. The computer-assisted method of claim 13, wherein the dynamic programming algorithm includes a global-local alignment algorithm.

15. The computer-assisted method of claim 9, wherein the step of determining the statistical significance of each alignment score to determine a best-fit alignment score includes the step of computing a z-score as the number of standard deviations above a mean score.

16. The computer-assisted method of claim 9, wherein the step of outputting to at least one output device the identity of such three-dimensional protein structure includes the step of displaying the three-dimensional protein structure on a visual display device.

17. A computer program, residing on a computer-readable medium, for assigning an amino acid probe sequence to a known three-dimensional protein structure, the computer program comprising instructions for causing a computer to:

(a) access a string describing the amino acid sequence of the probe sequence;

(b) generate, from the amino acid string, at least one sequence-derived property for the probe sequence, defined as $p_1, p_2 \ldots p_n$, wherein each p represents the sequence-derived property of a corresponding amino acid of the probe sequence;

(c) access a string $t_1, t_2 \ldots t_m$ of structural properties, wherein each t represents the structural property of a corresponding amino acid of the known three-dimensional protein, for each member of a library of known three-dimensional protein structures;

(d) execute an alignment algorithm to compute an alignment score indicating the optimal alignment of the string $p_1, p_2 \ldots p_n$ to the string $t_1, t_2 \ldots t_m$ by applying a combined compatibility function $g(p_i, t_j)$;

(e) determine the statistical significance of each alignment score to determine a best-fit alignment score; and (f) apply the best-fit alignment score to indicate or select the corresponding three-dimensional protein structure from the library for output to a user.

18. The computer program of claim 17, wherein each string $t_1, t_2 \ldots t_m$ of structural properties is determined from a known one-dimensional and three-dimensional structure of a protein.

19. The computer program of claim 17, wherein the combined compatibility function $g(p_i, t_j)$ is of the form:

$$g(p_i,t_j)=f(aa_{pi},t_j)+w \times h(p_i,t_j)$$

where $aa_{pi}$ is the amino acid type for $p_i$, w is a weighting factor, the function $f(aa_{pi}, t_j)$ is a compatibility function that relates the amino acid sequence of the probe sequence to structural properties of known three-dimensional protein structures, and the function $h(p_i, t_j)$ is an extended compatibility function that relates sequence-derived properties of the probe sequence to structural properties of known three-dimensional protein structures.

20. The computer program of claim 17, wherein the combined compatibility function $g(p_i, t_j)$ is of the form:

$$g(p_i, t_j) = w' \times \sum_{k=1}^{20} ma_{pi}[k] f(k, t_j) + w \times h(p_i, t_j)$$

where k is the amino acid type for $p_i$, w and w' are weighting factors, $ma_{pi}[k]$ denotes a weight assigned to amino acid of type k in $p_i$, the function $f(k,t_j)$ is a compatibility function that relates the amino acid sequence of the probe sequence to structural properties of known three-dimensional protein structures, and the function $h(p_i, t_j)$ is an extended compatibility function that relates sequence-derived properties of the probe sequence to structural properties of known three-dimensional protein structures.

21. The computer program of claim 17, wherein the alignment algorithm includes a dynamic programming algorithm.

22. The computer program of claim 21, wherein the dynamic programming algorithm includes a global-local alignment algorithm.

23. The computer program of claim 17, wherein the instructions for causing a computer to determine the statistical significance of each alignment score to determine a best-fit alignment score includes instructions for causing the computer to compute a z-score as the number of standard deviations above a mean score.

24. The computer program of claim 17, wherein the instructions for causing a computer to apply the best-fit alignment score to indicate or select the corresponding three-dimensional protein structure from the library for output to a user includes instructions for causing the computer to display the three-dimensional protein structure on a visual display device.

25. The computer assisted method of claim 1, wherein the at least one sequence derived property is a secondary structure of the amino acid sequence.

26. The computer assisted method of claim 9, wherein the at least one sequence-derived property is a secondary structure of the probe sequence.

27. The computer program of claim 17, wherein the at least one sequence-derived property is a secondary structure of the probe sequence.

* * * * *